(12) United States Patent
Vangeneugden et al.

(10) Patent No.: US 8,168,129 B2
(45) Date of Patent: May 1, 2012

(54) APPARATUS AND METHOD FOR PURIFICATION AND DISINFECTION OF LIQUID, SOLID OR GASEOUS SUBSTANCES

(75) Inventors: Dirk Vangeneugden, Opgrimbie (BE); Robby Jozef Martin Rego, Geel (BE); Danny Havermans, Beerse (BE); Herman Blok, Retie (BE)

(73) Assignee: Vlaamse Instelling Voor Technologisch Onderzoek (Vito), Mol (BE)

( * ) Notice: Subject to any disclaimer, the term of this patent is extended or adjusted under 35 U.S.C. 154(b) by 1017 days.

(21) Appl. No.: 11/913,034

(22) PCT Filed: May 2, 2006

(86) PCT No.: PCT/BE2006/000043
§ 371 (c)(1),
(2), (4) Date: May 19, 2008

(87) PCT Pub. No.: WO2006/116828
PCT Pub. Date: Nov. 9, 2006

(65) Prior Publication Data
US 2008/0292497 A1    Nov. 27, 2008

(30) Foreign Application Priority Data

Apr. 29, 2005 (EP) .................................... 05447095
Oct. 31, 2005 (EP) .................................... 05077494

(51) Int. Cl.
*A61L 2/00* (2006.01)
*B01J 19/08* (2006.01)
*H05F 3/00* (2006.01)
*H01J 27/00* (2006.01)

(52) U.S. Cl. ........... 422/186.04; 422/1; 422/22; 422/23; 204/164; 204/157.15; 204/193; 205/687; 250/426

(58) Field of Classification Search .......... 422/1, 22–23, 422/186.04; 204/164, 157.15, 193; 205/687; 250/426
See application file for complete search history.

(56) References Cited

U.S. PATENT DOCUMENTS
4,699,892 A    10/1987 Suzuki
(Continued)

FOREIGN PATENT DOCUMENTS
DE    199 51 117 A1    4/2001
(Continued)

OTHER PUBLICATIONS

Yamabe et al., "Water treatment using discharge on the surface of a bubble in water." *Plasma Processes and Polymers* 2:3(2005): 246-251.

(Continued)

*Primary Examiner* — Jill Warden
*Assistant Examiner* — Monzer Chorbaji
(74) *Attorney, Agent, or Firm* — Merchant & Gould P.C.

(57) ABSTRACT

An apparatus and method are for disinfection and purification of a liquid, gaseous or solid phase, or a mixture thereof. The apparatus includes: a central electrode, a dielectric layer adjacent to the electrode, a first area adjacent to the dielectric layer, and is configured to introduce a first medium into the first area, a second area adjacent to the first area. The apparatus is also configured to introduce a second medium into the second area, and for creating a plasma in the first medium, while the first medium is present in the first area, by applying a voltage between the first electrode and a second electrode. An injector injects the plasma into the second area, in order to be mixed with the second medium.

23 Claims, 7 Drawing Sheets

U.S. PATENT DOCUMENTS

| | | | |
|---|---|---|---|
| 5,100,596 A | | 3/1992 | Haag et al. |
| 5,635,059 A | | 6/1997 | Johnson |
| 5,876,663 A | * | 3/1999 | Laroussi .................. 422/23 |
| 6,558,638 B2 | | 5/2003 | Zadiraka et al. |
| 2002/0175068 A1 | | 11/2002 | Hammerstrom et al. |
| 2003/0101936 A1 | * | 6/2003 | Lee .................. 118/723 E |
| 2004/0007539 A1 | | 1/2004 | Denes et al. |
| 2004/0058799 A1 | | 3/2004 | Chau et al. |
| 2004/0237544 A1 | | 12/2004 | Ueno et al. |

FOREIGN PATENT DOCUMENTS

| | | | |
|---|---|---|---|
| EP | 0 481 660 A1 | | 4/1992 |
| EP | 1 053 976 A1 | | 11/2000 |
| JP | 60-129119 | | 7/1985 |
| JP | 06-321530 | | 11/1994 |
| WO | WO 93/17781 | | 9/1993 |
| WO | WO 96/12677 | | 5/1996 |
| WO | WO 99/47230 | * | 9/1999 |
| WO | WO 03/055285 A1 | | 12/2002 |
| WO | WO 2004/076052 A2 | | 9/2004 |

OTHER PUBLICATIONS

Hoeben, Wilhelmus Frederik Laurens Maria, *Pulsed corona-induced degradation of organic materials in water.* Technische Universiteit Eindhoven, 2000.

Grabowski et al., *Water cleaning by pulsed corona discharges.* Padova, Italy: Proc. Hakone IX, 2004.

Anpilov et al., "The effectiveness of a multi-spark electric discharge system in the destruction of microorganisms in domestic and industrial wastewaters." *J Water Health* 2:4(2004): 267-277.

Vroon et al., "Preparation and characterization of thin zeolite MFI membranes on porous supports." *Journal of Membrane Science* 144(1998): 65-76.

Kremer et al., "Preparation of Zeogrids through interposed stapling and fusion of MFI zeolite type nanoslabs." *Studies in Surface Science and Catalysis* 143(2002): 185-192.

* cited by examiner

APPARATUS AND METHOD FOR PURIFICATION AND DISINFECTION OF LIQUID, SOLID OR GASEOUS SUBSTANCES

FIELD OF THE INVENTION

The present invention is related to the use of atmospheric plasma and chemical photo-catalysis technology for treatment of liquids and/or gases. The invention is of interest in the fields of disinfection and purification of drinking water and industrial waste water, antifouling of industrial cooling water systems, remediation of polluted surface and ground water sites, bio-farming including hydro-culturing, and cleaning and disinfection of domestic and recreational water systems, such as e.g., swimming pools, showers and jacuzzis, ponds, etc.

Additionally the invention can be applied for the disinfection, cleaning and purification of gases, such as e.g., air, in domestic and industrial air-conditioning and air-treatment systems.

BACKGROUND OF THE INVENTION

Plasma technology has been pursued for treatment of liquids, such as e.g., water, for some time (Hoeben, 2000; Lee & Lee, 2003; Yamabe et al., 2004; Grabowski et al., 2004; Lambert & Kresnyak, 2000; Johnson, 1996, Johnson, 1997; Denes, 2004; Anpilov et al., 2004). The problem usually is to produce a homogeneous dielectric barrier discharge plasma with sufficient surface area in or above a liquid phase layer. The treatment that is usually associated with the generation of arcs, also called streamers, is referred to as Corona treatment rather than homogenous dielectric barrier discharge plasma treatment. Corona technology is often used in an air environment in combination with ozone or UV treatment in order to enhance the oxidative nature of the chemical reactions that take place during these processes. The generation of UV light, radicals, singlet oxygen, peroxides and oxidized species during these discharge processes is underlying the disinfection and purification of the liquid phase. However, to achieve sufficient mixing of these active species with the liquid phase that is to be treated is often a problem.

UV photo-catalysis is also used for disinfection and removal of micropollutants in liquids such as water. For this purpose, porous membranes or granulates can be loaded or coated with catalysts such as $TiO_2$. Under the influence of UV or visible light, catalyzed oxidative reactions can take place on the surface of a carrier. The products of such reactions have a strong disinfecting potential.

Although some toxic organic compounds may be destroyed using either Corona treatment or UV photo-catalysis, a wide variety of residual micropollutant species cannot be eliminated using these techniques.

Most commonly, water is disinfected using chemical additives such as chlorine or biocides. Known drawbacks are that such agents often are hampered in their efficiency to kill non-bacterial species or cause the formation of undesired side products such as organic halogens subject to absorption (AOX) through interaction of e.g., chlorine with organic matter in water. Furthermore, chlorine and biocides have a negative impact on the quality of drinking water. Also some rest chemical oxygen demand (COD) can cause in certain niches post-growth of bacteria and may lead to infection and fouling of equipment and utilities.

A number of technical problems are identified regarding the use of submerged plasma technology aimed at disinfection and purification of liquids, such as e.g., water, and also gases, such as e.g., air. A first problem is how to generate a dielectric barrier discharge (DBD) plasma in a gaseous phase which is submerged into or surrounded by a liquid phase.

The geometry and positioning of the electrodes as well as the way and conditions in which both phases are mixed with one another are crucial to obtain a homogeneous dielectric barrier discharge plasma within the mixed phase.

The importance of using a homogeneous dielectric barrier discharge plasma rather than a Corona discharge plasma is manifest for the efficiency and efficacy of treatment, energy consumption and wear of the electrodes in the plasma reactor.

A second problem related to the use of plasma technology that is directed towards disinfection and purification of liquid or gaseous media is often posed in the requirement for industrial capacity. Using state-of-the art treatment equipment, practical limitations are often observed with flow rates of substrate liquid or gas streams. As a consequence, energy costs of operation and up scaling costs to meet capacity requirements may be high.

A problem associated with photo-catalyzed micropollutant removal processes is the degeneration of the catalyst that is used. This requires regeneration, or sometimes even replacement, of the catalyst involving downtime and extra costs for replacement of the catalyst. Documents U.S. Pat. Nos. 5,876, 663 and 6,558,638 suffer from a number of the problems described above. In particular, the U.S. Pat. No. 6,558,638 reference describes a system wherein a plasma is produced in water. In this system, a tube is provided, produced from a dielectric material, and surrounded by a number of ring electrodes. This apparatus is submerged in the liquid to be treated, normally water. Air is pumped through the dielectric tube, and enters the water through apertures in the dielectric tube. The plasma discharge zone is present between the successive ring electrodes, i.e. plasma is created outside the tube volume, in the water and/or in the air bubbles entering the water. One electrode may have an elongate portion extending in the centre of the dielectric tube, but this is not an essential element: this central portion merely helps to decrease the capacitance of the first interelectrode gap (on the outside of the tube), and to thereby put a maximum portion of the voltage on said first gap, and then cause a sequence of successive breakdowns ('slipping surface' discharge). This technique has a number of drawbacks, the main one being a loss of power due to the existence of current in the water. This system also suffers from the fact that the flow of liquid through the apparatus is subjected to considerable flow restrictions, which puts a limit on the possible flow rates which can be processed. This system is also difficult to up-scale, due to its specific geometry, wherein the electrical field is coaxial to the flow direction of the treated liquid.

AIM OF THE INVENTION

The present invention aims to provide a method and apparatus which does not suffer from the drawbacks of prior art systems.

SUMMARY OF THE INVENTION

The present invention is related to an apparatus and method as described in the appended claims. The apparatus and method employ the use of atmospheric multi-phasic controlled injection discharge (AMPCID) plasma technology which may be combined with photo-catalysis in order to achieve a synergistic effect on disinfection and purification, i.e., on removal of residual micropollutants, in media such as e.g., water and air. According to the method of the invention, plasma is generated in a first phase, which is preferably a gaseous phase, which is thereafter mixed with a second phase, such as e.g., a liquid phase. UV light and/or visible light may be co-produced with the plasma itself and may after transport to the second phase induce photo-catalysis. Although the main focus of this invention is on water and/or air treatment, the scope of applications is not limited to these preferred media but also includes organic media, such as e.g., oils and hydrocarbon containing liquids, mixtures of aqueous solutions with organic phases, and gases other than air, such as e.g., hydrogen, nitrogen, oxygen, ozone, carbon dioxide, helium, argon, etc., as well as mixtures thereof.

The present invention employs a multi-phasic principle whereby high throughput processing of both liquid and gaseous phases are not hampered by flow rate restrictions. Moreover the multi-phasic concept is modular and can be easily up-scaled to meet higher throughput requirements.

The present invention enables the use of plasma technology in combination with photo-catalysis, thereby making optimal use of the synergy between both processes with regard to regeneration of the catalyst as well as overall energy consumption. Chemically activated species and radicals are produced within the plasma that are directly or indirectly consumed by the photo-induced catalysis reaction. The catalysis reaction may take place directly on a surface proximally exposed to the generated plasma, or, remotely at a certain distance from the generated plasma. The efficiency and efficacy of treatment will in the latter case be dependent on the one hand on the lifespan of the formed chemical species and the distance that they need to travel to reach the catalytic zone, and on the other hand on the spectral characteristics of the generated plasma and the absorbance of the light by the matrices it encounters in the pathway between its origin and the catalytic zone.

Through employing UV and/or visible light-transparent phase-separators between the multiple phases, the present invention may additionally exploit the synergy of the combined use of plasma generation and photo-catalysis. The UV and visible light produced during the dielectric plasma discharge can either be used directly for disinfection and purification or indirectly to regenerate the photo-catalyst.

DETAILED DESCRIPTION OF THE INVENTION

The invention is related to an apparatus for disinfection and purification of a medium comprising a liquid, gaseous or solid phase, or a mixture thereof, and to a method performed with said apparatus, in which plasma is generated under atmospheric conditions in a first medium which is preferably a gaseous phase, such as e.g., air, which is then introduced by injection into a second medium, which is preferably a liquid phase, such as e.g., water, in such a way, that a mixing flow between the first and the second medium is established and the plasma is utilized to disinfect and purify the first and/or the second medium.

Figure 1:
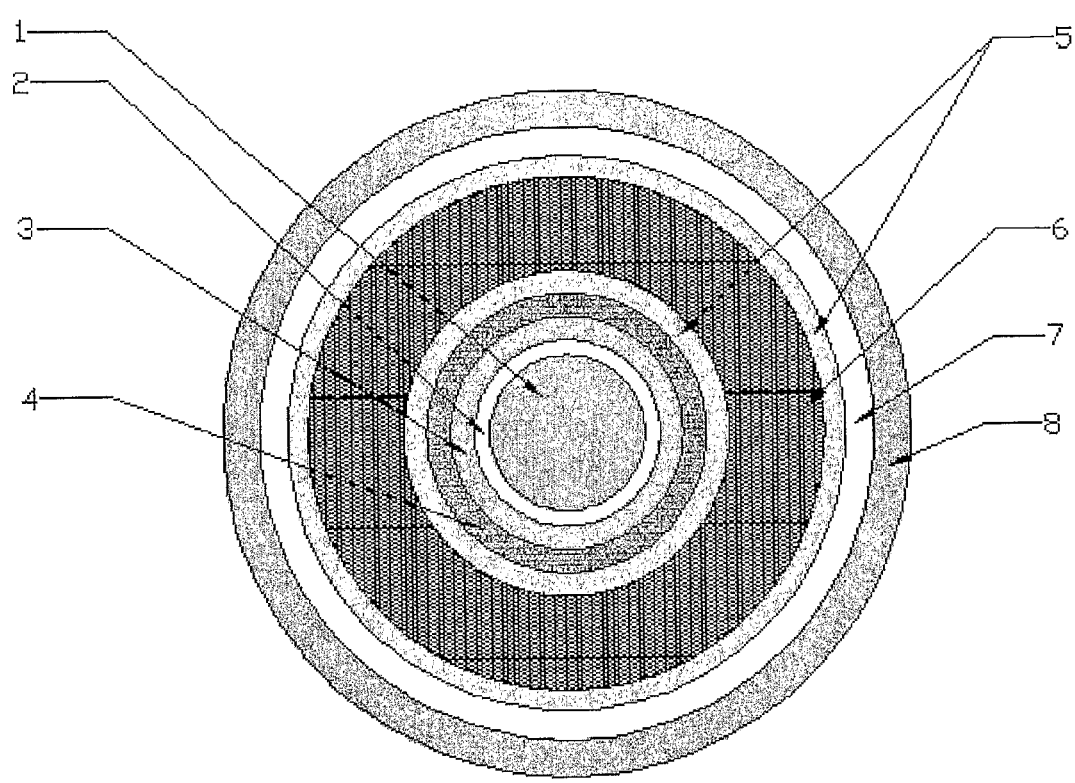
FIG. 1 illustrates a sectioned view of a tubular reactor according to the invention.
Figure 8:
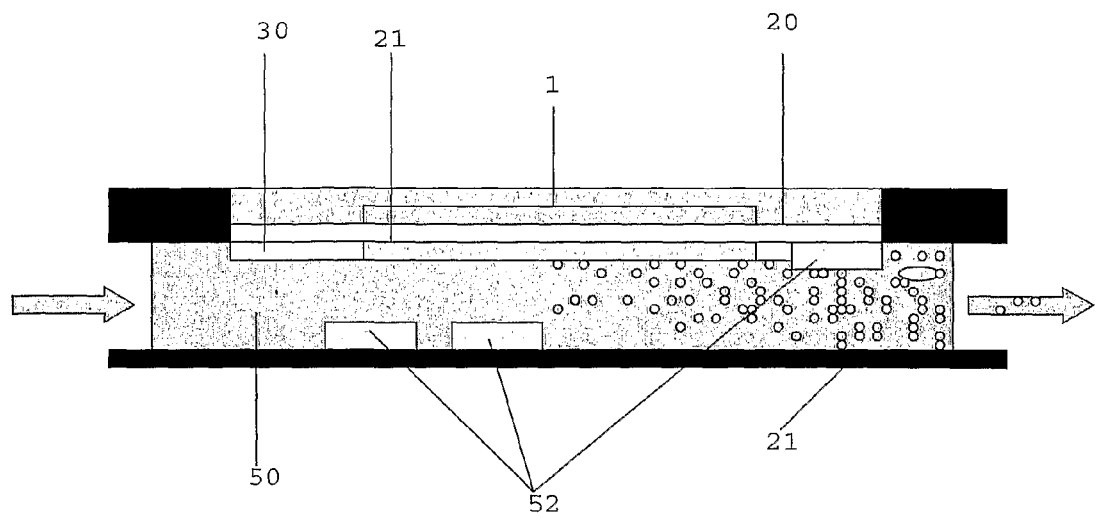
FIGS. 8 and 9 show views of an asymmetrical panel-shaped reactor according to the invention.
Figure 9:
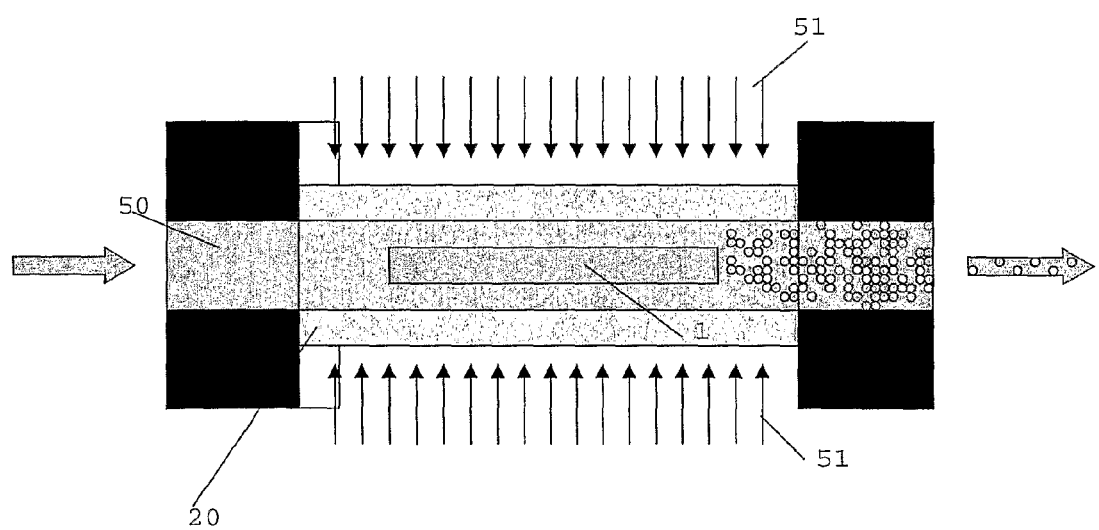

FIG. 1 shows a cross-section of a first embodiment of the apparatus of the invention, hereafter also called a reactor, having a tubular geometry. Other geometries are equally possible, however, such as the planar (flat panel) geometry shown in FIG. 6-9. The geometries of FIGS. 1-6 are symmetric, comprising a central round or flat electrode surrounded by a number of areas, to be described hereafter. FIGS. 8-9 show an asymmetric embodiment, equally to be described further in this description.

Figure 2:
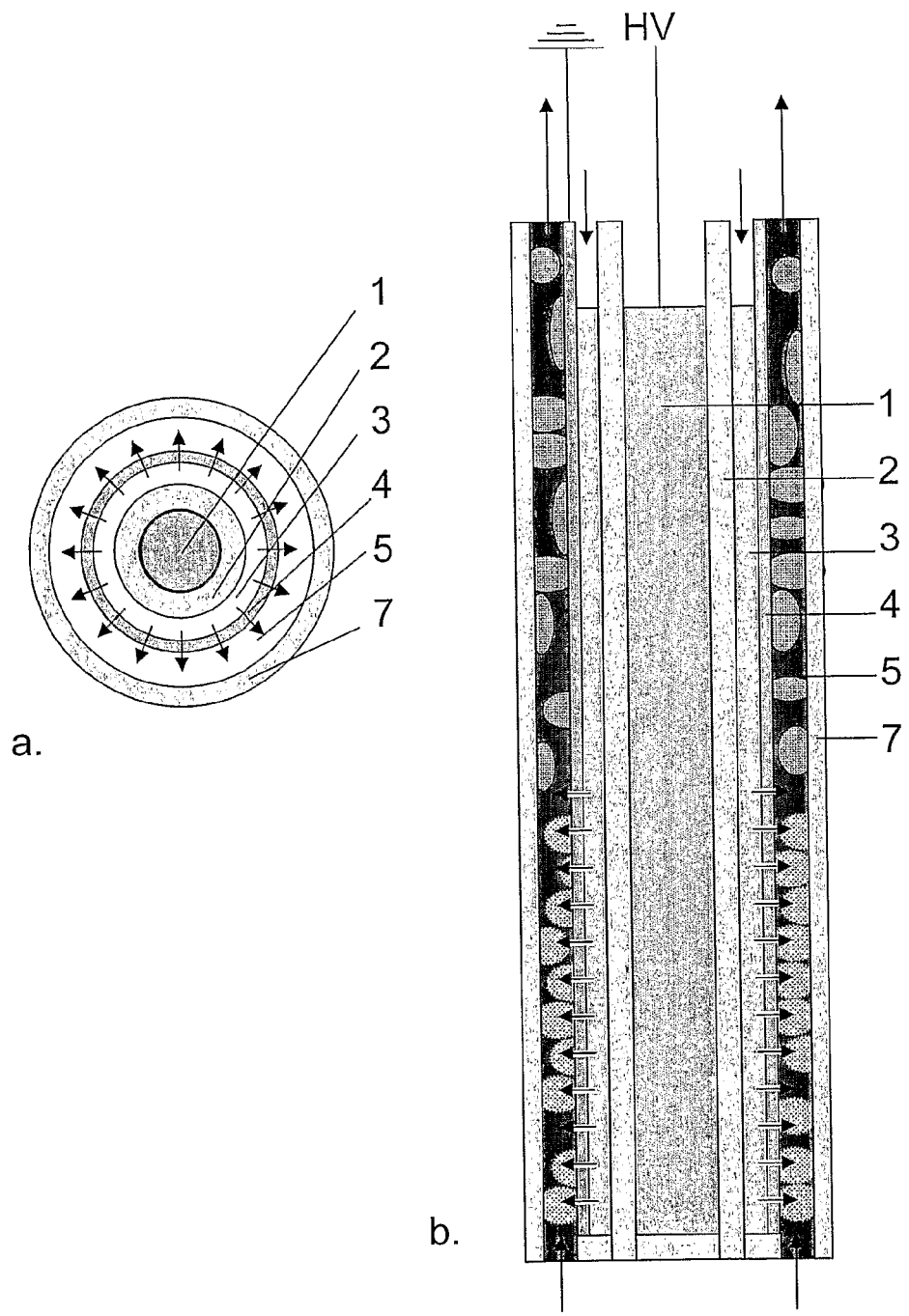
FIG. 2 is a side view of the reactor of FIG. 1.

We now refer however to the first embodiment of a tubular reactor, shown in FIGS. 1 and 2. The following general description comprises both apparatus features and method features, as will be apparent from the applied wording. The main characteristic of the tubular apparatus according to the invention, is that is comprises at least a central electrode 1, surrounded by a dielectric layer 2, in contact with the electrode. The electrode 1 and dielectric barrier layer 2 are centrally placed in an area 3 in which the first medium, preferably a gaseous phase, is introduced (see arrows at the top or area 3). The gaseous phase in area 3 is contained by a plasma generation vessel, whose boundaries act as a permeable separating wall 4 acting as a phase separator, allowing the passage (through pores or holes) of the first medium into a surrounding area 5, which is arranged to contain the second medium, preferably a liquid phase, and which is surrounded by an outer barrier zone 7. The liquid phase in the embodiment of FIG. 2 flows through the area 5 (see arrows), and is treated during said flow. In other configurations, the second medium may be treated in batch mode, by introducing a fixed volume of the medium into area 5 and treating said volume. In special configurations, the reactor can also operate without the phase separator (explained further with reference to the embodiment of FIGS. 8 and 9).

According to the preferred embodiment of FIG. 2, there is only one actual electrode 1, while the liquid in area 5 is sufficiently conductive and plays the part of the second electrode, preferably connected to ground. For example, if the liquid to be treated is water from a public distribution network, this water stream is grounded, and when it is present in the area 5, it will act as a counterelectrode. It is not necessary in that case for the parts 4 or 7 which are in contact with the water, to be conductive. If the liquid itself is not grounded or not connected to a suitable reference, the phase separator 4 is preferably produced from a conductive material, and may be connected to ground or to said reference, as shown in FIG. 2. In this setup, the phase separator and the liquid in area 5 act as the second electrode during operation of the reactor.

The apparatus further comprises means to apply a suitable voltage between the main electrode 1 and the 'liquid' electrode, for creating a plasma in the first medium, present in area 3. According to the method of the invention, this plasma is then injected with or without the phase separator into the liquid in area 5 to thus purify said liquid.

The question whether or not the liquid can be used as the second electrode, depends on the conductivity of said liquid. Water is mostly sufficiently conductive to play this part. However, in case the liquid is insufficiently conductive, a second physical, preferably grounded electrode 8 may be applied around the barrier zone 7 (see FIGS. 3 and 4) or it may replace the outer barrier zone 7 and be arranged in direct contact with the liquid in area 5 (FIG. 5). This also helps to enhance and generate additional plasma in the gaseous phase/liquid phase zone in area 5. In the case of FIG. 5, the liquid in area 5 may also be conductive, and play the part (together with electrode 8) of the second electrode. The phase separator 4 may then be conducting or not.

If the phase separator 4 is used, it may consist of a non-conducting material, such as a porous membrane, e.g. a ceramic membrane, or a capillary membrane or a glass or quartz tube that is porous or that contains capillaries. Alternatively, the phase separator 4 may be produced from a non-conducting material such as ceramic, glass, quartz, or a polymer into which orifices of a well-defined geometry are introduced in discrete areas or over the whole surface of the phase separator 4 according to a certain pattern to allow a controlled flow of gas from compartment 3 into area 5 that contains the second medium, which is preferably a liquid phase, but which also may be a gaseous or solid phase, or a mixture thereof.

Alternatively, the phase separator 4 may consist of a conducting material, such as e.g., stainless steel, containing pores, capillaries or orifices.

In case the second medium is a liquid or gaseous phase, it may additionally contain a solid, or sol-gel phase, which may be porous or solid, acting as a carrier material, and which may be loaded or coated with a photo-catalytic moiety, or with nano-particles containing photo-catalytic moieties, such as e.g., $TiO_2$, $CaBi_2O_4$, or $PbBi_2Nb_2O_9$. The catalytic activity may either be contained within area 5 within a permeable net or basket in a zone 6 (see FIG. 1) which may be placed proximal or contiguous to a phase separator 4, or, it may be contained within the whole area 5, which is then filled with a porous carrier material, or, alternatively, it may be coated into or onto the phase separator 4 and/or on the outer barrier zone 7. In all cases the solid or porous phase containing the carrier material should permit the passage of light and/or activated chemical species from the plasma. The surface area of the carrier onto which the catalyst is provided is preferably large to increase the interaction, on the one hand with the UV- and reactive species from the remote plasma that feed the catalysis, and on the other hand with the second medium that is to be treated and that serves as a substrate for oxidative catalysis.

Alternatively, the catalyst may be supplied within the capillaries or pores of the phase separator 4 material itself. Because of the capillary forces, the liquid phase is absorbed into the porous or capillary phase separator material. In case the second medium is a liquid phase, it can however not pass through the pores or capillaries into the first, gaseous phase unless a relatively large pressure difference between the gaseous and the liquid phase is applied. The content of the pores or capillaries can be periodically purged in a synchronous manner with plasma generation by pulsing the pressure in the gaseous phase above the critical pressure value.

The phase separator 4 material should in either case both be plasma- and chemically compatible for the reaction products that are generated within the catalytic zone. Additionally it is desirable that the carrier material is transparent under submerged conditions for the remotely generated UV and visible light by the plasma to maximize the conversion yields of the photo-catalysis reactions. Such a material might be porous quarts or porous aluminum oxide and may contain both aligned straight-through-going parallel pores or non-straight, branched through-going pores.

In case the second medium is a solid phase, it may additionally contain another solid, or sol-gel phase, which may be porous or solid, and which may be loaded or coated with a photo-catalytic moiety. The catalytic activity may either be contained within the whole area 5, or partially within sections of it, in all cases permitting the passage of light and/or activated chemical species from the plasma, or it may be coated into or onto the phase separator 4 and/or on the outer barrier zone 7.

As mentioned already, the whole system may be enclosed by a counter electrode 8 which may be grounded. In between electrode 8 and area 5 that contains the second medium an outer barrier zone 7 may be present. The outer barrier zone 7 may, depending on the material used, either function as a dielectric barrier layer, or it may simply just determine the outer boundaries of the device. In any case and in all configurations, the system should contain at least one electrode that is surrounded by a dielectric barrier zone in order to prevent streaming plasmas which result in increased wear of the electrodes.

Plasma is initially generated in the first medium, which is a gaseous phase, in area 3, in a continuous or pulsed mode, and is then introduced into the second medium. In case the second medium is a fluid, the liquid or gaseous phase may either be treated batch wise within a closed system, or it may be pumped into the reactor in a parallel or cross flow manner relative to the flow that contains the first medium, i.e., the (preferably) gaseous phase. A combination of batch wise treatment of the second medium with internal circulation is also possible.

In a preferred embodiment the second medium is a liquid phase which is grounded and used as an earthed electrode if it is conducting. The liquid phase is prevented from entering area 3, e.g., by applying an overpressure in area 3 and possibly in combination with the use of orifices, capillaries or pores with controlled dimensions and/or material properties. Depending on the placement of the electrodes, grounding of the electrodes and the presence or absence of dielectric barriers, geometry of the reactor, ionic state of the second medium and process conditions such as electrical regime and flow rate of the first and second medium, plasma in the first, gaseous phase may continue to live, or even be enhanced, for a certain period of time while it is injected into the second medium. In the latter case one can speak of a sustained atmospheric multi-phasic controlled injection discharge (AMP-CID) plasma generation. In the bubble which is subsequently formed highly reactive species from the plasma will react with the second medium at the surface interface between the first medium and the second medium while it is dissolving into the second medium (if both mediums completely dissolve in each other, one probably obtains the highest treatment efficiency).

Figure 6:
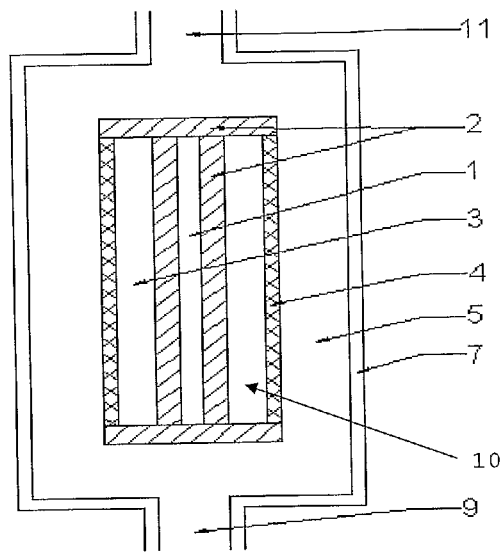
FIGS. 6 and 7 show views of a panel-shaped reactor according to the invention.

A top view schematic drawing of a symmetric flat panel implementation of the principle is shown in FIG. 6. The second, preferably liquid phase is pumped through inlet 9 into the reaction chamber and enters area 5 where it is exposed to and mixed with the first medium, preferably a gaseous phase, which is injected into compartments 3 and 10, which may be connected to one another. Centrally placed is an electrode 1 surrounded by a dielectric barrier layer 2. The first, gaseous phase in which plasma is generated in compartments 3 and 10 is injected into the second, preferably liquid phase in area 5 e.g., by applying an overpressure in compartments 3 and 10 relative to area 5. The treated second phase is leaving the reaction chamber through outlet 11. For batch wise (closed circuit) treatment of the second phase the in and outlets of the system may be closed by valves (not shown).

Figure 7:
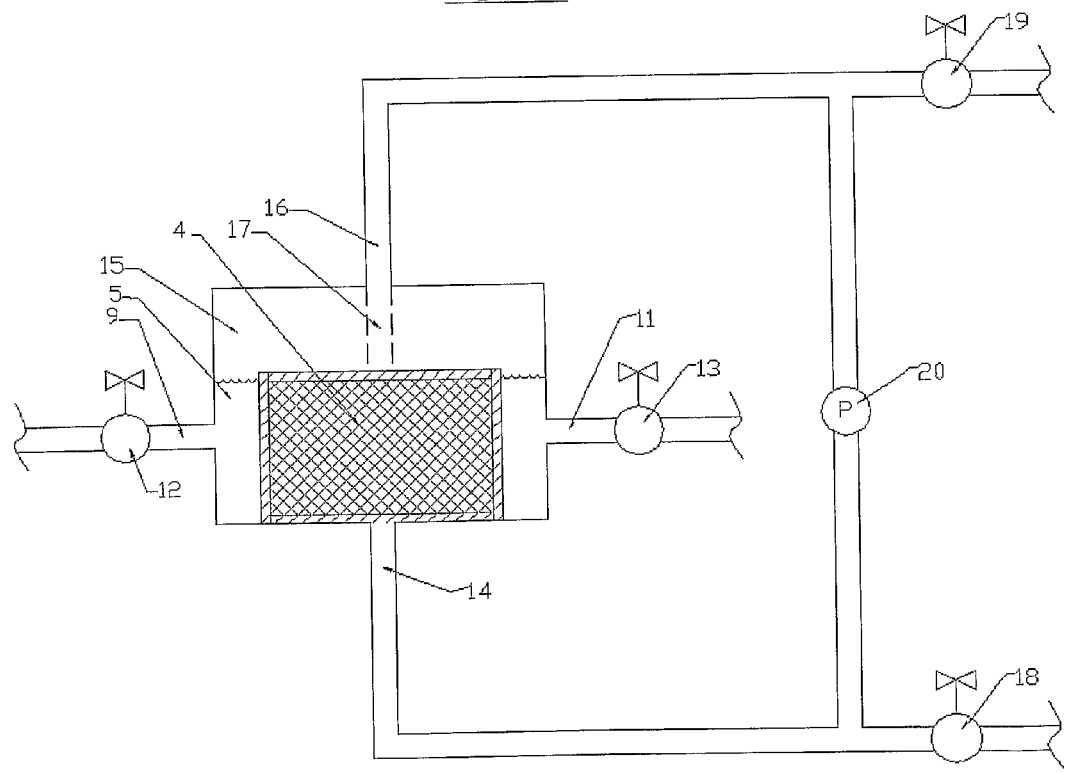

A side view of a flat panel implementation of the same principle is shown in FIG. 7. The second, preferably liquid phase is pumped into the reaction chamber through inlet 9 into area 5. Inlet 9 and outlet 11 can be optionally closed by respectively valves 12 and 13 for batch treatment of the second medium. Plasma is generated within the first, gaseous phase and the said active species are mixed with the second medium. The first, gaseous phase is injected into the reaction chamber through inlet 14. The gaseous phase is collected from compartments 3, 10 and 15, and guided through a collecting device 16 into outlet 17. Inlet 14 and outlet 17 may be closed by valves 18 and 19 respectively for batch treatment of the gaseous phase. A closed system is obtained in which the gaseous phase can be re-used and recycled by using pump 20 to transport the gaseous phase from outlet 17 into inlet 14 again. The pump 20 also acts as the means for applying an overpressure to the gaseous phase in area 3, so that the plasma created in this phase, may be injected into area 5. Such a means for injecting the plasma is present in any embodiment according to the invention. In general, the 'means for injecting the plasma' in an apparatus of the invention is understood to comprise at least such a pumping means, and possibly the phase separator 4 (if present).

For both tubular and flat panel configurations, the first and second phases are separated after plasma treatment. Both the first medium and the second medium, if it is a fluid, can be independently processed in a closed (batch or closed circuit) or in an open (flow-through) system. With a closed system, the liquid and/or gaseous mediums are continuously recycled and pumped back into the multi-phasic plasma treatment device. With an open flow-through configuration, a single pass through the reactor is achieved and a high flow throughput processing can be realized.

FIGS. 8 and 9 show a side and top view of another embodiment of the apparatus of the invention, which is an asymmetric embodiment, comprising—as in the previous embodiments—an electrode 1, and a dielectric layer 20 adjacent and in contact with said electrode. In this embodiment however, the dielectric is present to one side only of the electrode. The compartment wherein the second medium, preferably a liquid is present (in circulating or batch mode), is directly adjacent to the dielectric layer, but a means is present to pump the first medium, preferably a gas, in which plasma 21 is to be created, into an area 30 between the dielectricum and the liquid. In this embodiment, there is no separating wall between the areas 30 and 50. The gas is pumped into area 30 from both sides of the electrode, as is visible in FIG. 9, in order to sustain an overpressure in said area 30, so that a separate gas area 30 is maintained during operation of the apparatus. Under these conditions, the voltage is applied between the first electrode 1 and the second electrode, formed by the conductive liquid in area 50 and/or by providing a preferably grounded second electrode at the bottom of the apparatus (not shown). In this embodiment, the liquid is preferably conductive, so that the liquid body itself actually serves as the second electrode, and the plasma is maintained primarily in the area 30, after which it is injected into area 50, through the pressure difference between areas 30 and 50. A closed system can be obtained in which the gaseous phase can be re-used and recycled by pumping it again in the reaction chamber through inlet 51. Obstructions 52 may be present for optimal gas/liquid mixing. These obstructions can have any suitable form, to cause a non-laminar flow of liquid through the reactor, and to thus obtain said optimal mixing.

The advantages of the present invention are:

The multi-phasic plasma reactor concept is modular and suitable for up scaling to (industrial) higher throughput applications.

Because of its modularity, different chemical photo-catalysts formulations can be easily exchanged, tested and used depending on the application and type of liquid or gaseous medium to be treated.

In the multi-phasic plasma device both gaseous and liquid mediums can be disinfected or purified using either a continuous or batch mode of operation, for either or both mediums.

The process underlying the plasma-assisted photo-catalysis in the treatment system has many controllable parameters and features. For instance, one can choose the gas, liquid or solid phases, or mixtures thereof, to obtain optimal results for different applications; flow rates of both liquid and gaseous phases can be varied in a wide dynamic range; electrical conditions, such as frequency, potential difference, power and pulsed or continuous mode of operation, can be varied; the geometry and placement of the electrodes and dielectric barrier layers as well as orifices, capillaries or pores within the phase separator is flexible; operating the multi-phasic system in combination with other orthogonal and conventional disinfection and purification methods, such as e.g. UV treatment, ozone or peroxide treatment, or treatment with metal particles, such as e.g., Ag, is possible without having to rebuild or redesign the reactor or process.

Robust and simple design facilitates maintenance and increases life time of the reactor while minimizing operational downtime. Depending on the choice of materials used electrode wear can be minimal and costs for material replacement can be kept low. For instance, a system consisting of a centrally placed electrode 1 (FIG. 1), consisting of e.g., an aluminum strip or closely packed metal powder, which is surrounded by a dielectric barrier layer 2, such as eg. ceramic, and which is placed into e.g., a quartz tube with provided small through-going orifices, can be robust in operation and requires little or no maintenance for a biphasic water-air stream treatment when contained by a dielectric material 7, such as e.g., quartz or glass.

An additional advantage of using transparent materials such as glass or quartz is that the plasma process is visible and can be inspected and monitored throughout the whole system.

The concept enables the treatment of the first medium which may contain a plurality of different gases, or, alternatively, the second, preferably liquid phase can be simultaneously treated with a plurality of different gases. An example is given in FIG. 2, in which the first, gaseous phase contains two different gases residing respectively in area 3 and 10. A binary activation or deactivation system may be obtained in this case when the two gases are selected and used in an antagonistic or agonistic manner respectively. For instance, a catalytic reaction may occur when the first, gaseous phase containing a gas A (injected into area 3) and containing a gas B (injected into compartment 10), gas A and gas B being reactive to one another, or to the consecutively formed intermediates between either gas and the second medium, come in contact and mix with one another at a location such as e.g., the outlet 11 in FIG. 2. The principle of using a plurality of different gases is of course also applicable to a tubular geometry. Additionally, instead of a parallel treatment system one might also use a serial treatment system in which a plurality of different gases is sequentially introduced into a serial array of different plasma reactors.

The concept allows the use of a tubular as well as a flat panel geometry. A tubular design offers advantages regarding manufacturing, up scaling and energy consumption of the system.

Energy (light) and chemical reactive species generated from plasma can be continuously recycled and regenerated in the chemical catalysis process. This process is sustainable with respect to the environment and overall energy consumption.

The disinfection and purification process does not rely on additives such as chlorine or biocides to the second, preferably liquid phase to be treated. It is thus also from this point of view sustainable and environmentally friendly.

In case the second medium is a liquid phase, the gaseous phase (or phases) may be contained within a closed system in order to more effectively disinfect the liquid phase enabling process conditions to be directed towards higher yields of chemical species that are generated such as e.g., ozone. Ozone is not directly released into the environment as a gas, but will be partially taken up and dissolved to a certain extend into the liquid phase where it has a remote disinfection capacity; the main fraction of the gaseous phase(s) may be recycled and contained within the closed system.

In the multi-phasic plasma treatment device liquid phases, that may additionally contain catalytic moieties incorporated into solid phase carrier materials, may also consist of organic media, or mixtures of inorganic and organic media. The organic phases, or mixtures of inorganic and organic phases can then serve as a substrate for plasma-assisted photo-catalysis.

The efficiency, efficacy and destructive power of the present invention with regard to residual and persistent organic pollutants (POP) may be devastating compared to any other known state-of-the-art techniques because of the synergistic combination of several contributing complementary effects such as e.g., UV-irradiation, radical formation, formation of other (derivatized) chemical species exhibiting strong oxidative properties, localized heating effects, acoustic effects caused by imploding pulsed-plasma-induced bubbles and catalytic conversion processes that are linked to plasma generation.

The system of the invention does not suffer from power loss due to current in the liquid, because the plasma is not created in the liquid itself, but in a gas phase, after which the plasma is injected in the liquid. This also causes a lower breakdown voltage (typically 0.1-6 kV for tubular and 0.1-25 kV for flat panel configurations) to be observed in systems according to the invention, compared to prior art systems.

In comparison with the system of U.S. Pat. No. 6,558,638, the apparatus of the invention has less flow restrictions for the liquid to be treated.

The electrical field created in the apparatus of the invention is perpendicular to the treated liquid's flow direction. This makes it easier to up-scale the apparatus by simply making it longer.

MODES FOR CARRYING OUT THE INVENTION

There are several modes of carrying out the present invention. The different concepts employ multi-phasic systems that have an enabling and synergistic effect with regard to disinfection and purification potential as well as to overall energy consumption and material wear. The modus operandi of the present invention may be in a tubular or in a flat panel geometry. The embodiments already referred to above, are hereafter described in additional detail.

In a first preferred embodiment the principle is reduced to a tubular geometry (FIG. 2). In FIGS. 2a and 2b a top view and a side view of the system is shown respectively. A centrally placed high voltage electrode 1 is surrounded by a dielectric barrier tube 2. The dielectric barrier layer consists preferably of non-porous ceramic, glass or quartz. This element is again centrally placed into a tube 4 with a larger diameter. The tube is preferably made of a conducting material such as stainless steel and serves as a grounded electrode and phase separator 4. Into area 3, gas is injected. The tube contains orifices, capillaries or pores at the lower bottom part through which the gas is pumped into area 5, which is contained by a dielectric barrier tube 7 with a larger diameter surrounding phase separator 4. A liquid, such as water, is injected in area 5, preferably in a cross flow manner relatively to the gas stream which is introduced in area 3. Alternatively, in stead of liquid, gas or mixtures of gas and liquid may also be injected into area 5. Plasma is generated in area 3 in a continuous or pulsed mode. The liquid, gas, or liquid/gas mixture pumped in area 5 is treated by injecting the generated plasma from area 3 through phase separator 4 into area 5. Area 5 may contain additional zones 6 into which catalysts, preferably photo-catalysts, such as $TiO_2$ are incorporated, that can further contribute to the treatment (not shown in FIG. 2).

Figure 3:
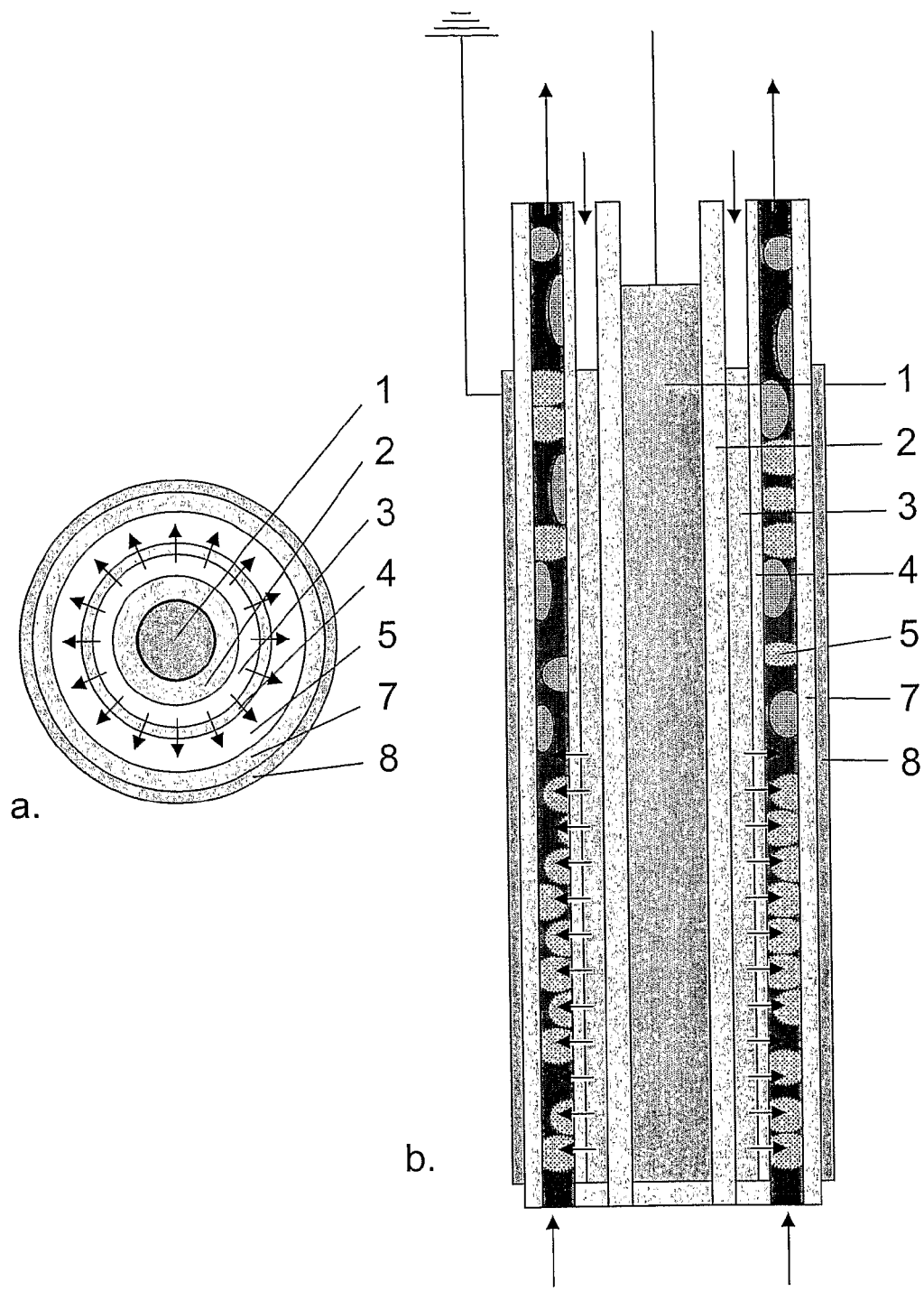
FIGS. 3 to 5 shows other embodiments of a tubular reactor according to the invention.

In a second preferred embodiment a second high voltage electrode 8 is introduced in the system as described above in the first preferred embodiment in order to enhance and generate additional plasma in the gaseous phase/liquid phase zone in area 5 (FIG. 3). In FIGS. 3a and 3b a top view and a side view of the system is shown respectively.

Figure 4:
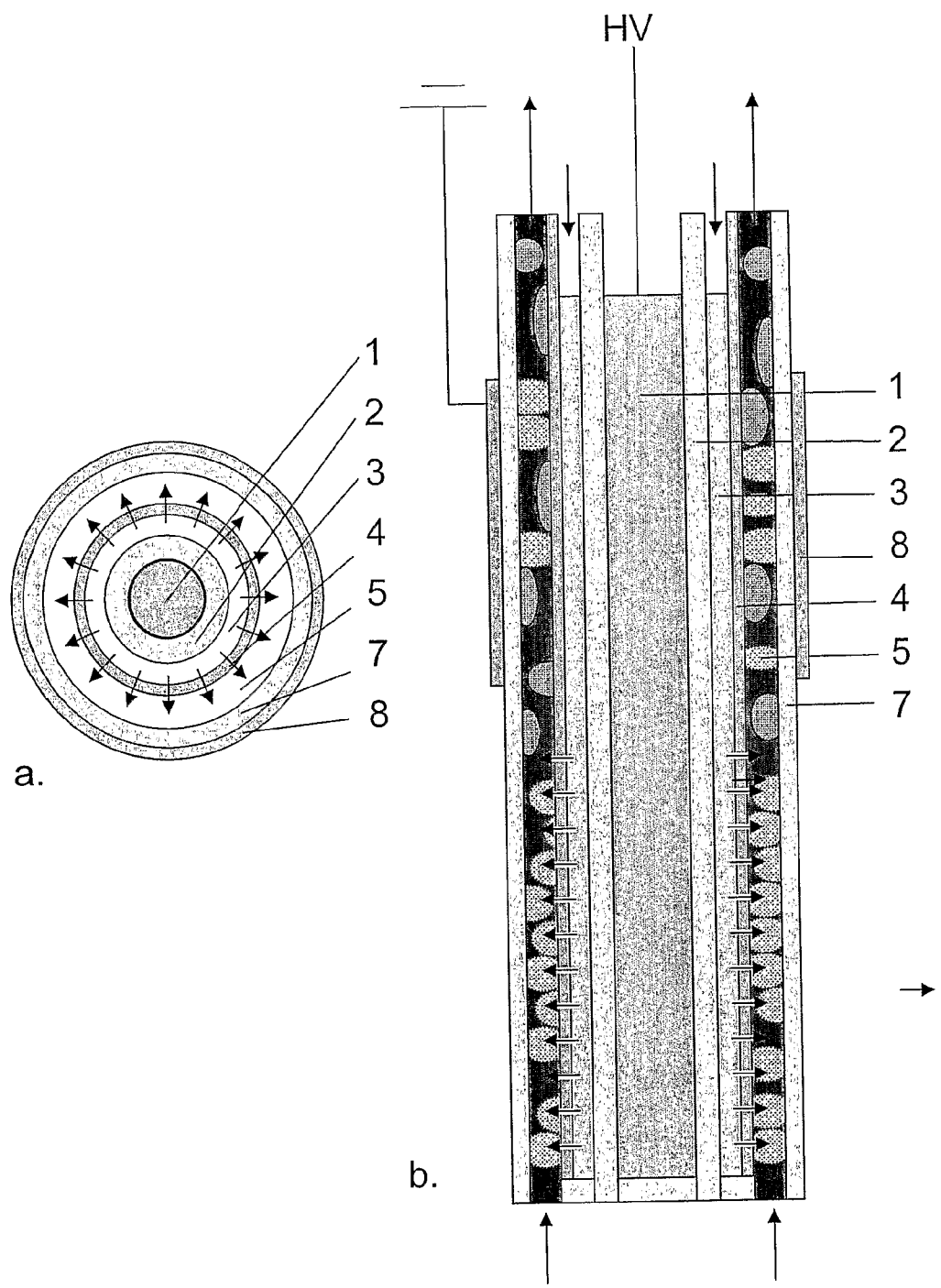
Figure 5:
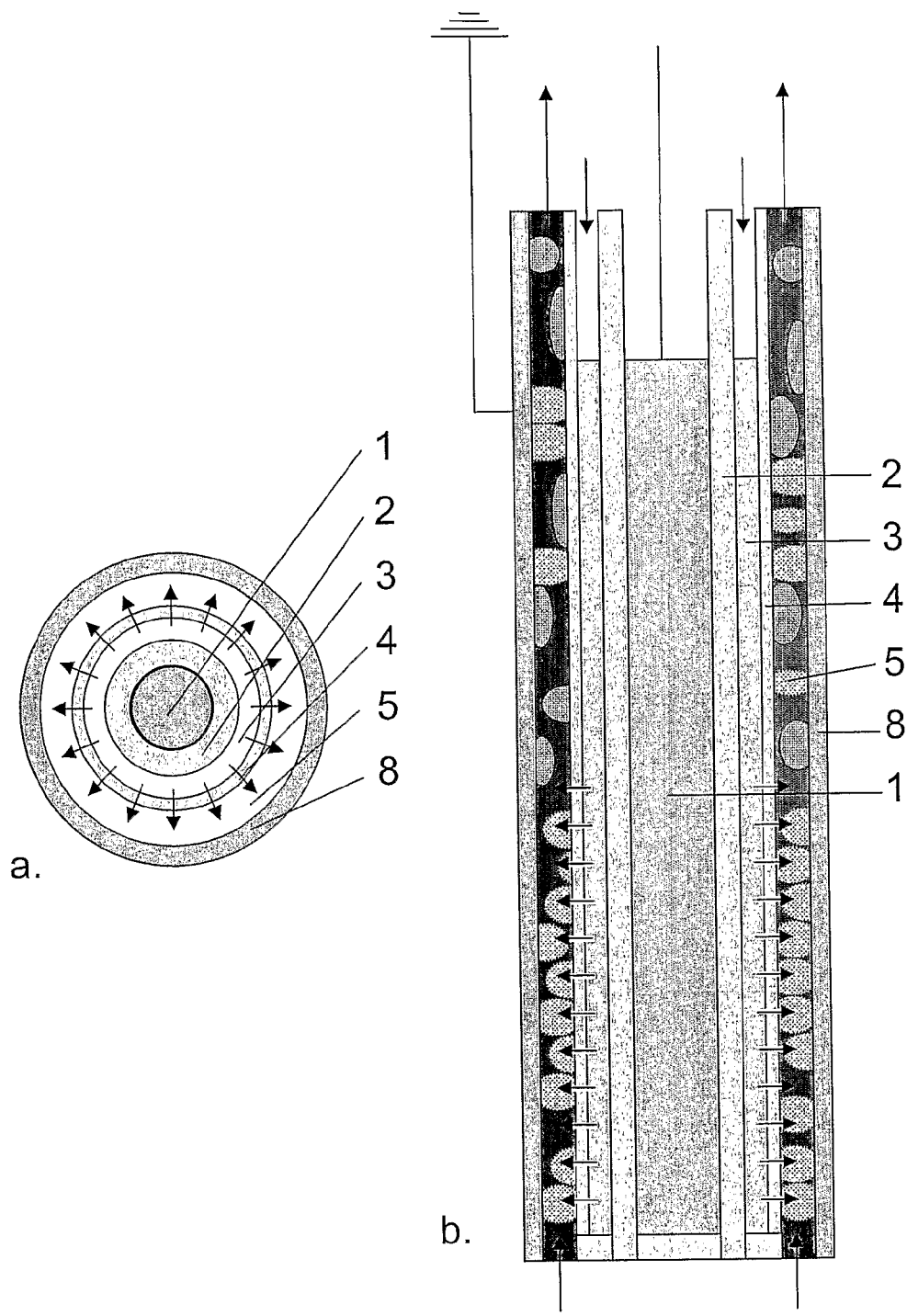

In a third preferred embodiment the second high voltage electrode 8 is placed downstream over some distance from the area where the separator phase 4 contains orifices, capillaries or pores and where the gaseous phase is injected into the liquid phase (FIG. 4). This may prevent the formation of plasma streamer discharges in area 5 at locations juxtaposed to the orifices, capillaries or pores in phase separator 4 where the gaseous phase is injected into the liquid phase. In FIGS. 4a and 4b a top view and a side view of the system is shown respectively.

In a fourth preferred embodiment the system is similar to the system as shown in FIG. 4, except that the dielectric barrier layer 7 is omitted (FIG. 5). In FIGS. 5a and 5b a top view and a side view of the system is shown respectively.

The invention claimed is:

1. An apparatus for disinfection and purification of a medium comprising a liquid, gaseous or solid phase, or a mixture thereof, said apparatus comprising:
    a first electrode,
    a dielectric layer adjacent to said first electrode,
    a first area adjacent to said dielectric layer, and means for introducing a first medium into said first area,
    a second area adjacent to said first area, and means for introducing a second medium into said second area,
    means for creating a plasma in said first medium, while said first medium is present in the first area, by applying a voltage between said first electrode and a second electrode,
    means for injecting said plasma into the second area, to be mixed with the second medium.

2. The apparatus according to claim 1, wherein said dielectric layer and said first area are surrounding said first electrode, and said second area is surrounding said first area.

3. The apparatus according to claim 1, wherein said means for injecting said plasma includes a separating wall in between said two areas, said wall comprising orifices on at least a part of its surface.

4. The apparatus according to claim 3, wherein said first area is formed by a reactor vessel in which the first electrode is centrally placed, and wherein the separating wall is the outer wall of said reactor vessel, and wherein the second area is delimited by a barrier wall, arranged around said reactor vessel.

5. The apparatus according to claim 3, wherein said separating wall is produced from a porous material, said orifices being formed by the pores of said material.

6. The apparatus according to claim 3, wherein said separating wall is produced from a non-porous material and wherein orifices are made in said material on the whole or a part of the surface of the separating wall.

7. The apparatus according to claim 1, wherein said dielectric layer is arranged adjacent said electrode and in contact with said electrode.

8. The apparatus according to claim 1, wherein said means for creating a plasma discharge are arranged for creating a plasma discharge between said first electrode and the second medium, when said second medium is present in the second area, said second medium acting as the second electrode.

9. The apparatus according to claim 1, wherein said second electrode is adjacent to the second area, and wherein said means for creating a plasma discharge are arranged for creating said discharge between the first electrode and said second electrode.

10. The apparatus according to claim 1, wherein said second area further comprises a carrier material capable of producing photo-catalytic activity.

11. The apparatus according to claim 10, wherein said carrier material is contained in a net or basket arranged in the second area.

12. The apparatus according to claim 10, wherein said carrier material is coated into or onto at least a part of the separating wall.

13. The apparatus according to claim 1, said apparatus having a tubular geometry.

14. The apparatus according to claim 1, said apparatus having a planar geometry.

15. The apparatus according to claim 14, wherein said apparatus has a symmetric structure, comprising a central planar electrode, and two dielectric layers adjacent each side of said electrode, and the first area comprising two sub-areas adjacent to said dielectric layers, and the second area being adjacent to said first area.

16. The apparatus according to claim 14, wherein said apparatus has an asymmetric structure, comprising a planar electrode, and one dielectric layer adjacent to said electrode, and the first area adjacent to said electrode, and the second area adjacent to said first area.

17. The apparatus according to claim 16, wherein no separating wall is present between the first and second area, and wherein the means for injecting the plasma comprises means for pumping said first medium into said first area with sufficient pressure to maintain said first area during operation of the apparatus.

18. A method for treating a medium comprising a liquid, gaseous or solid phase, or a mixture thereof, comprising the steps of:
providing an apparatus for disinfection and purification of a medium comprising a liquid, gaseous or solid phase, or a mixture thereof, said apparatus comprising:
a first electrode,
a dielectric layer adjacent to said first electrode,
a first area adjacent to said dielectric layer, and means for introducing a first medium into said first area,
a second area adjacent to said first area, and means for introducing a second medium into said second area,
means for creating a plasma in said first medium, while said first medium is resent in the first area, by applying a voltage between said first electrode and a second electrode,
means for injecting said plasma into the second area to be mixed with the second medium,
introducing the first medium into the first area of said apparatus,
introducing the second medium into the second area of said apparatus,
creating a plasma in said first medium, while said first medium is in the first area,
injecting said plasma into the second area.

19. The method according to claim 18, wherein said first medium is a gaseous medium.

20. The method according to claim 18, wherein said plasma is created under atmospheric conditions.

21. The method according to claim 18, wherein the second medium flows through the second area, and is treated during said flow.

22. The method according to claim 18, wherein said second medium is treated in batch mode, wherein a volume of said second medium is introduced into said second area, after which said volume is treated.

23. The method according to claim 18, wherein no separation wall is present between said first and second areas, and wherein said first medium is introduced in the first area between said first electrode and said second area, with sufficient pressure to maintain said first area during the creation of said plasma.

* * * * *